United States Patent [19]

Ohta et al.

[11] Patent Number: 5,336,679
[45] Date of Patent: Aug. 9, 1994

[54] TETRAHYDROIMIDAZOPYRIDINE DERIVATIVES AND SALTS THEREOF

[75] Inventors: Mitsuaki Ohta; Takeshi Suzuki; Jun-ya Ohmori; Keiji Miyata, all of Ibaraki; Isao Yanagisawa, Tokyo, all of Japan

[73] Assignee: Yamanouchi Pharmaceutical Co., Ltd., Tokyo, Japan

[21] Appl. No.: 955,735

[22] PCT Filed: May 23, 1991

[86] PCT No.: PCT/JP91/00689
§ 371 Date: Jan. 15, 1993
§ 102(e) Date: Jan. 15, 1993

[87] PCT Pub. No.: WO91/18900
PCT Pub. Date: Dec. 12, 1991

[30] Foreign Application Priority Data

May 25, 1990 [JP] Japan .................. 2-135850

[51] Int. Cl.$^5$ .................. C07D 471/04; A61K 31/44
[52] U.S. Cl. .................. 514/300; 546/121
[58] Field of Search .................. 546/121; 514/300

[56] References Cited

U.S. PATENT DOCUMENTS 4,588,732 5/1986 Browne .................. 546/121

Primary Examiner—Bernard Dentz
Attorney, Agent, or Firm—Burgess, Ryan & Wayne

[57] ABSTRACT

Tetrahydroimidazopyridine derivatives which are useful for the treatment of irritable bowel syndrome are provided and can be represented by the following formula,

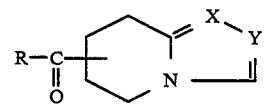

wherein either one of X and Y is nitrogen and the other one is a radical represented by the formula $=C(R^1)-$; and R is a radical of the formula

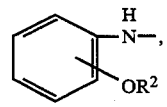

a radical of the formula

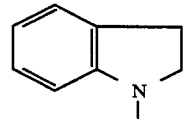

or a radical of the formula

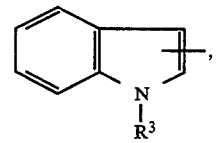

in which $R^1$, $R^2$ and $R^3$ are same or different and represent hydrogen or a $C_1-C_6$ alkyl group, and salts thereof. Pharmaceutical compositions are also provided.

9 Claims, No Drawings

TETRAHYDROIMIDAZOPYRIDINE DERIVATIVES AND SALTS THEREOF

FIELD OF THE INVENTION

This invention relates to tetrahydroimidazopyridine derivatives and salts thereof which are useful as medicines.

The compounds of this invention and salts thereof are considered to be useful for the prevention and treatment of the syndrome of hypersensitive intestinal diseases (irritable bowel syndrome) and the like.

BACKGROUND TECHNIQUES

As a result of intensive studies on the compounds having the antagonism against 5-HT$_3$ receptor, tile present inventors discovered that the compounds represented by the above-mentioned general formula are novel compounds having a high degree of antagonism against 5-HT$_3$ receptor, and accomplished this invention on the basis of these findings.

DISCLOSURE OF THE INVENTION

The term "lower" described in this specification means, unless otherwise specified, a linear or branched carbon chain having a carbon number of 1 to 6. Accordingly, as examples of the "lower alkyl group" may be mentioned methyl, ethyl, propyl, isopropyl, butyl, isobutyl, tertbutyl, pentyl, isopentyl, hexyl, 1-methylpentyl, 2-methylpentyl and 2-ethylbutyl groups. Of these, the groups having a carbon number of 1 to 3, such as methyl, ethyl and propyl groups are the most preferable.

In addition, some of the compounds of this invention can form salts, and this invention also includes the salts of the compounds represented by the above-mentioned general formula (I). As examples of these salts, may be mentioned salts with an inorganic base (such as sodium and potassium), salts with an organic base (such as ethylamine, propylamine, diethylamine, triethylamine, morpholine, piperidine, N-ethylpiperidine, diethanolamine and cyclohexylamine), salts with a basic amino acid (such as lysine and ornithine), ammonium salts, salts with a mineral acid (such as hydrochloric, sulfuric, phosphoric and hydrobromic acids), salts with an organic acid (such as acetic, oxalic, succinic, citric, maleic, malic, fumaric, tartaric and methanesulfonic acids), and salts with an acidic amino acid (such as glutamic and aspattic acids).

Furthermore, the compounds of this invention contain an asymmetric carbon atom in the molecule, and the compounds represented by the general formula (I) include all kinds of isomers based on this asymmetric atom, such as optically active compounds, rasemic compounds and diastereomers.

Preparative Methods

Described below are the typical preparative methods for the compounds of this invention.

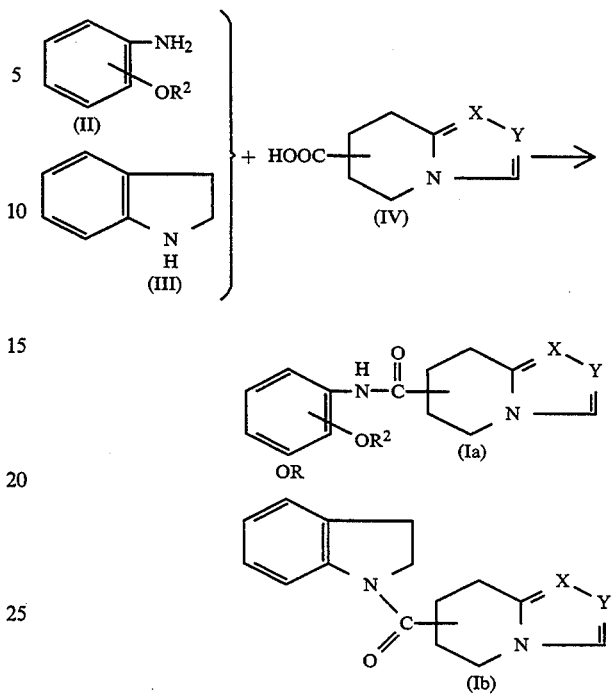

The compounds of this invention represented by the general formula (Ia) or (Ib) can be obtained by the reaction of an aniline derivative represented by the general formula (II), or 2,3-dihydroindole represented by the formula (III), with a carboxylic acid represented by the general formula (Iv) or a reactive derivative thereof.

This reaction is an amide-forming reaction, and hence a variety of well-known methods may be applicable. There is no specific limitation upon the kind of solvent to be used, insofar as it is inert to the reaction. As Examples of the solvent to be used, may be mentioned dioxane, diethyl ether, tetrahydrofuran, chloroform, ethyl acetate and diemtylformamide, etc.

The compound (Iv) may be directly used for the reaction with the compound (II) or the compound (III), or may be used for that reaction in the form of a reactive, carboxy derivative in some cases.

When the compound (IV) itself is used for the reaction, any condensation agent commonly employed may be applicable (such as N,N-dicyclohexylcarbodiimide).

As examples of the reactive, carboxy derivative of compound (IV), may be mentioned acid halides, acid anhydride, acid azide, and various active esters employed for peptide synthesis.

The reaction should preferably be carried out in the presence of a base in some cases, depending on the type of the reactive derivative of compound (IV) used. As examples of the base used in this case, may be mentioned inorganic bases (such as sodium bicarbonate, potassium bicarbonate, sodium carbonate and potassium carbonate) and organic bases (such as triethylamine, diisopropylethylamine, dimethylaniline and pyridine).

The compound (II) or compound (III) is generally used for the reaction in this form, but may also be used, as required, in the form of an alakali metal salt for the reaction with the reactive derivative of compound (IV).

The amount of compound (II) or (III) to be used for the reaction should preferably be at least equimolar to the amount of compound (IV) or its reactive derivative.

The reaction may be carried out under cooling, at room temperature or under heating depending on the type of amide formation reaction adopted, but is generally carried out under cooling or at room temperature.

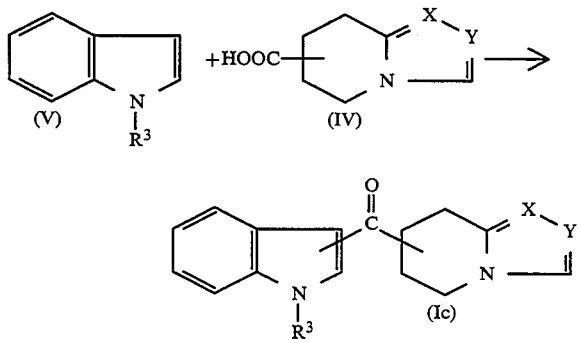

The compounds of this invention represented by the general formula (Ic) can be obtained by the reaction of a compound represented by the general formula (V) with a carboxylic acid represented by the general formula (IV) or a reactive derivative thereof.

This is a reaction for the synthesis of carbonyl compounds using a carboxylic acid or a derivative thereof, and hence a variety of well-known methods are applicable.

When a carboxylic acid compound (IV) itself is used, dehydrocondensation reaction with a compound (V) is adopted, in which polyphosphoric acid, for example, is used as the condensation agent. This reaction may be carried out in the absence of solvent, or may also be carried out by using a solvent, wherein there is no specific limitation upon the kind of solvent to be used insofar as it is inert to the reaction. In general, a solvent having a proper boiling point is used, with the reaction temperature being taken into consideration. As examples of the solvent to be used, may be mentioned decalin, tetralin and diglyme, and the reaction is carried out at room temperature or preferably under heating.

When an acid halide of compound (IV) is used, Friedel-Crafts acylation reaction is adopted. This is a well-known reaction including many variations. In this case, is used a Lewis acid as catalyst, such as aluminum chloride, ferric chloride, tin chloride, trifluoroboric acid-diethyl ether complex and titanium tetrachloride. Any kind of solvent may be used insofar as it is inert to the reaction, but a preferable one should be selected depending on the type of Lewis acid used (such as acetonitrile and carbon disulfide). The reaction is carried out at room temperature or preferably under heating.

When an acid amide of compound (IV) is used, Vilsmeyer reaction is adopted. This is also a well-known reaction frequently employed for the synthesis of heterocyclic carbonyl compounds. As the reagent for converting the amide into Vilsmeyer complex, may be generally used an ordinary halogenating agent, such as phosphorus pentachloride and phosphorus oxychloride. This reaction may be carried out in the absence of solvent, or may also be carried out by using a solvent, wherein there is no specific limitation upon the kind of solvent to be used insofar as it is inert to the reaction. As a typical example of the solvent, may be mentioned 1,2-dichloroethane.

The reaction is carried out at room temperature or preferably under heating.

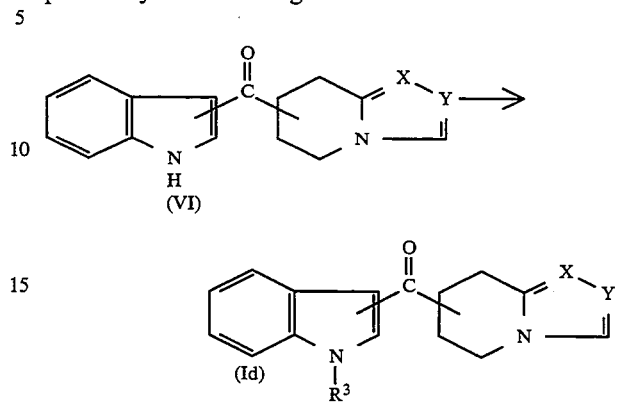

This is an N alkylation reaction, and a variety of well-known methods may be applicable.

As an example of N-alkylation, may be mentioned direct N-alkylation using an alkylating agent. In this case, the reaction may be carried out under cooling, at room temperature or under heating, but is preferably carried out under cooling or at room temperature. There is no specific imitation upon the kind of solvent to be used insofar it is inert to the reaction. As examples of proper solvent, may be mentioned dioxane and dimethylformamide. The reaction is carried out in the presence of a base, or the amino group in the compound (VI) is previously converted into an alkali metal salt and then subjected to N-alkylation reaction.

As examples of the alkylating agent, may be mentioned alkyl halides and alkyl sulfates. As examples of the base, may be mentioned inorganic bases (such as sodium bicarbonate, potassium bicarbonate, sodium carbonate and potassium carbonate), and organic bases (such as triethylamine, diisopropylamine, dimethylaniline and pyridine).

The compounds of this invention thus prepared are isolated and purified in the free form or as salts thereof. The isolation and purification are performed through oridinary chemical operations, such as extraction, crystallization, recrystallization and various types of chromatography.

Racemic compounds can be converted into pure stereoisomers by using a proper starting compound or by the ordinary racemic resolution method for example, a method of conversion into the diastereomer salt with an optically active salt (e.g., tartaric acid) followed by optical resolution).

Effects Achieved by the Invention

The compounds of this invention and salts thereof specifically prevented the temporary, slow pulse in anesthetized rats caused by serotonin, and are therefore considered to have antagonism against 5-HT$_3$. Accordingly the compounds of this invention are considerd be effective for preventing the irritable bowel syndrome and the like, The pharmacological effects of the compounds of this invention were demonstrated by the methods described below.

1) Antagonism against 5-HT$_3$ Receptor

A male Wistar rat nine weeks old was anesthetized by intraperitoneal administration of 1 g/Kg urethane, and the blood pressure and heart rate were measured while practicing artificial respiration. The temporary decrease in the heart rate and the fall of blood pressure caused by intravenous administration of serotonin, or 2-methylserotonin which is a selective agonist against 5-HT$_3$, were recognized as the index of a reaction through the 5-HT$_3$ receptor [Bezold-Jarish Reflex; Paintal, A. S. Physiol. Rev., 53, 159 (1973)]

A compound of this invention or a salt thereof, if administered intravenously (0.03 to 3 μg/Kg) 10 minutes before the administration of serotonin or 2-methylserotonin, or administered orally (1 to 30 μg/Kg) 60 minutes before, prevented the decrease in the heart rate and the fall of blood pressure caused by serotonin or 2-methylserotonin in a degree depending on the dosage.

2) Prevention of Vomit Caused by Carcinostatic Agents

3) Prevention of Stress Feces Excretion

A male Wistar rat nine weeks old was put in a restrictive cage, and the number of excreted feces was measured. A compound of this invention or a salt thereof, if administered intravenously (1 to 100 μg/Kg), prevented the acceleration of defecation caused by the restrictive stress in a degree depending on the dosage.

In addition, tile compounds of this invention are low in toxicity.

Pharmaceutical preparations containing, as active ingredient, one or two kinds or more kinds of the compounds of this invention or salts thereof (tablets, powders, beadlets, capsules, pills, solutions, injections, suppositories, ointments and adhesive plasters, etc.) are prepared by the use of a carrier, an excipient and other additives commonly employed, and are administered orally (including sublingual administration) or parenterally.

As the carrier and excipient for pharmaceutical manufacturing, are used solid or liquid, nonpoisonous materials. As examples of such materials, may be mentioned lactose, magnesium stearate, starch, talc, gelatin, agar, pectin, gum arabic, olive oil, sesame oil, cacao butter, ethylene glycol and other materials commonly employed.

The clinical dosage of the compounds of this invention is properly determined by taking the illness conditions, the body weight, the age, the sex distinction and other factors of the patient being treated, but the proper daily dosage for adults is generally 0.1 to 10 mg for intravenous injection and 0.5 to 50 mg for oral administration, which is administered all at once or is subdivided in several doses.

EXAMPLES

The following Examples will further illustrate the invention. In addition, the preparative methods of the starting materials used in these Examples are described in Reference Examples.

REFERENCE EXAMPLE 1

A. Sulfate of methyl imidazo[1,5-a]pyridin-6-yl-carboxylate

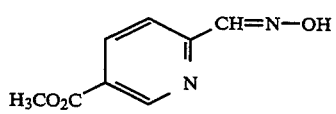

Sodium acetate (4.77 g) and hydroxylamine hydrochloride (4.04 g) were added to 30 ml methanol, and the mixture was stirred at room temperature for 30 minutes. The salts thus formed were removed by filtration, 3.20 g of methyl 6-formylnicotinate was added to the filtrate, and the mixture was stirred overnight at room temperature. After distilling off the solvent from the reaction mixture under reduced pressure, an aqueous solution of potassium carbonate was added, and the resulting mixture was extracted with a mixture of chloroform and isopropanol. The organic layer collected was dried over anhydrous magnesium sulfate, and the solvents were distilled off from the dried solution under reduced pressure, thus giving 3.21 g of methyl 6-hydroxyiminonicotinate as solid product.

Physicochemical Properties (i) NMR spectrum (CDCl-CD$_3$OD) δ: 4.00 (s, 3H), 7.95 (d, 1H), 8.20 (s, 1H), 8.35 (dd, 1H), 9.15 (d, 1H)

(ii) Mass spectrum (EI): m/z 180(M+)

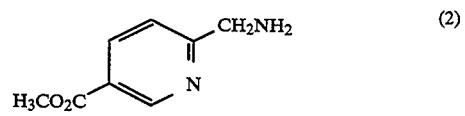

The compound obtained in (1) above (3.16 g) was added to a mixture of 34 ml water and 51 ml acetic acid, and 5.73 g of zinc powder was then slowly added under ice-water cooling. The mixture was stirred for 30 minutes, the insoluble matters were filtered off by using Celite, the filtrate was concentrated to dryness under reduced pressure, an aqueous solution of sodium carbonate was added to the residue, and the mixture was extracted with chloroform. The organic layer collected was dried over anhydrous magnesium sulfate, and the solvent was distilled off from the dried solution under reduced pressure, thus giving 2.90 g of oily methyl 6-aminomethylnicotinate.

Physicochemical Properties (i) NMR spectrum (CDCl$_3$) δ: 3.95 (s, 3H), 4.05 (s, 2H), 7.35 (d, 1H), 8.25 (dd, 1H), 9.15 (d, 1H)

(ii) Mass spectrum (EI): m/z 166(M+)

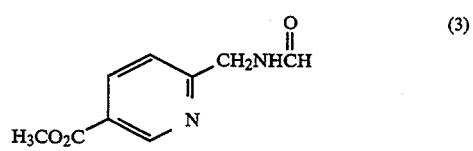

The compound obtained in (2) above (2.80 g) was added to 20 ml formic acid, and the mixture was stirred overnight at 100° C. and then concentrated to dryness under reduced pressure. An aqueous solution of sodium carbonate was added to the residue, the mixture was extracted with chlororform, the organic layer collected was dried over anhydrous magnesium sulfate, and the solvent was distilled off from the dried solution under reduced pressure. The residue was washed with diethyl ether, thus giving 2.07 g of methyl 6-formylaminomethylnicotinate as solid product.

Physicochemical Properties (i) NMR spectrum (CDCl$_3$) δ: 3.95 (s, 3H), 4.65 (d, 2H), 7.30 (d, 1H), 8.25 (dd, 1H), 8.35 (s, 1H), 9.15 (d, 1H)

(ii) Mass spectrum (EI): m/z 194(M+)

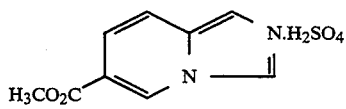
(4)

The compound obtained in (3) above (2.05 g) was added to 15 ml dichloroethane, 2.0 ml of phosphorus oxychloride was then added, and the mixture was heated under reflux for one hour, The reaction mixture was concentrated under reduced pressure, an aquous solution of sodium bicarbonate was added to the concentrate, and the mixture was extracted with chloroform. The organic layer collected was dried over anhydrous magnesium sulfate, the solvent was distilled off from the dried solution under reduced pressure, and the residue was washed with diethyl ether, thus giving 1.79 g of methyl imidazo[1,5-a]pyridine-6-carboxylate.

Physicochemical Properties (i) NMR spectrum (CDCl$_3$) δ: 3.94 (s, 3H), 7.20 (dd, 1H), 7.45 (d, 1H), 7.46 (s, 1H), 8.22 (s, 1H), 8.74 (d, 1H)
(ii) Mass spectrum (EI): m/z 176(M+)

This compound was then treated with equimolar sulfuric acid in ethanol, thus giving 2.51 g of sulfate of methyl imidazo[1,5-a]pyridin-6-yl-carboxylate.

Physicochemical Properties (i) Elemental analysis (as C$_9$H$_8$N$_2$O$_2$·H$_2$SO$_4$)

|  | C(%) | H(%) | N(%) | S(%) |
|---|---|---|---|---|
| Calcd. | 39.42 | 3.68 | 10.21 | 11.69 |
| Obsd. | 39.71 | 3.59 | 9.99 | 11.51 |

(ii) NMR spectrum(DMSO-d$_6$) δ: 3.90 (s, 3H), 7.45 (dd, 1H), 7.90 (s, 1H), 8.05 (s, 1H), 9.30 (d, 1H), 9.55 (s, 1H)
(iii) Mass spectrum (EI): m/z 176(M+, in the free from)

B. Methyl 5,6,7,8-tetrahydroimidazo[1,5-a]pyridine-6-carboxylate

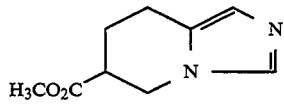

The sulfate of methyl imidazo[1,5-a]pyridine-6-carboxylate obtained in A above (2.19 g), 5% paradium-carbon(0.7 g) and acetic acid (30 ml) were put in a 100-ml autoclave, and the mixture was stirred overnight at 70° C. under a hydrogen gas pressure of 65 atmospheres. The insoluble matters were filtered off from the reaction mixture by using Cerite, the filtrate was concentrated to dryness under reduced pressure, an aqueous solution of sodium carbonate was added to the residue, and the resulting mixture was extracted with chloroform. The organic layer collected was dried over anhydrous magnesium sulfate, and the solvent was distilled off from the dried solution under reduced pressure, thus giving 1.4 g of methyl 5,6,7,8-tetrahydroimidazo[1,5-a]pyridine-6-carboxylate as solid product.

Physicochemical Properties (i) NMR spectrum (CDCl$_3$) δ: 1.70–2.10 (m, 1H). 2.10–2.40 (m, 1H), 2.50–3.10 (m, 3H), 3.70 (s, 3H), 3.95–4.40 (m, 2H), 6.75 (bs, 1H), 7.40 (bs, 1H)
(ii) Mass spectrum (EI): m/z 180(M+)

C. Hydrochloride of 5,6,7,8-tetrahydroimidazo[1,5-a]-pyridine-6-carboxylic acid

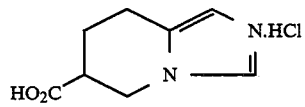

A mixture of the compound obtained in B above (1.4 g), 15 ml water and 5 ml concentrated hydrochloric acid was stirred overnight at 100° C., the reaction mixture was concentrated to dryness under reduced pressure, and the residue was washed with acetone, thus giving 1.35 g of hydrochloride of 5,6,7,8-tetrahydroimidazo[1,5-a]pyridin-6-carboxylic acid as solid product.

Physicochemical Properties (i) NMR spectrum (DMSO-d$_6$) δ: 1.9–2.3 (m, 2H), 2.75–3.0 (m, 2H), 3.0–3.3 (m, 1H), 4.1–4.6 (m, 2H), 7.4 (s, 1H), 9.1 (s, 1H
(ii) Mass spectrum (EI): m/z 166(M+ in the free form)

REFERENCE EXAMPLE 2

Synthesis of hydrochloride of 1-methyl-5,6,7,8-tetrahydroimidazo[1,5-a]pyridine-7-carboxylic acid A. Ethyl 1-methyl-5,6,7,8-tetrahydroimidazo[1,5-a]pyridine-7-carboxylate

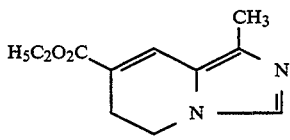
(1)

Ethyl 4-chlorobutyrate (7.0 g) was added at room temperature to a solution of 5-methyl-4-imidazole-carbaldehyde (4.17 g) and 60% oily sodium hydride (2.0 g) in 50 ml dimethylformamide (prepared by stirring at 50° C. for one hour). The resulting mixture was heated at 70° C. for four hours and then concentrated to dryness under reduced ressure, water was added to the residue, and the mixture was extracted with ethyl acetate. The organic layer collected was washed with water and then with saturated aqueous solution of sodium chloride, and dried over anhydrous magnesium sulfate. The dried solution was concentrated to dryness under reduced pressure, and the residue was subjected to column chromatography on silica gel (80 g). Elution with ethyl acetate gave 2.35 g (28%) of an about 1:1 mixture of 1-(3-ethoxycarbonylpropyl)-5-methyl-4-imidazole-carbaldehyde and 1-(3-ethoxylcarbonylpropyl)-4-methyl-5-imidazole-carbaldehyde.

Physicochemical Properties (i) NMR Spectrum(CDCl$_3$) δ: 1.25 (3H, t, J=7Hz), 1.85–2.70 (4H, m), 2.49, 2.52 (3H for all, s for each), 3.80–4.50 (4H, m), 7.40, 7.48 (1H for all, s for each), 9.71, 9.80 (1H for all, s for each)

60% Oily sodium hydrice (0.45 g) was added to a mixture comprising 2.23 g of the mixture of 1-(3-ethoxycarbonypropyl)- 5-methyl-4-imidazole-carbaldehyde and 1-(3-ethoxycarbonylpropyl)-4-methyl-5-imidazole-carbaldehyde obtained above, 3 g of molecular sieves (4A) and 30 ml toluene at a temperature of 110° C., and the resulting mixture was stirred at the same temperature for six hours. The reaction mixture was filtered, the filtrate was concentrated to dryness under reduced pressure, the residue was subjected to column chromatography on silica gel (30 g), and elution with ethyl acetate gave 0.85 g of ethyl 1-methyl-5,6-dihydroimidazo[1,5-a ]pyridine-7-carboxylate.

Physicochemical Properties (i) NMR spectrum (CDCl₃) δ: 1.34 (3H, t, J=7Hz), 2.32 (3H, s), 2.53–3.01 (2H, m), 3.85–4.50 (4H, m), 7.40 (1H, s), 7.48 (1H, s)

(ii) Mass spectrum (EI): m/z 206(M+)

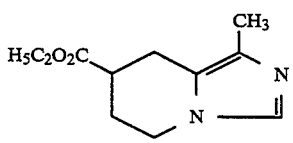
(2)

Ethyl 1-methyl-5,6-dihydroimidazo[1,5-a]pyridine-7-carboxylate (0.90 g) was subjected to catalytic reduction in 30 ml methanol at room temperature for ten hours by using 0.02 g of 5% paradium-carbon as the catalyst. The reaction mixture was filtered, the filtrate was concentrated to dryness under reduced pressure, ethyl acetate was added to the residue, and the resulting mixture was extracted with 0.5N-HCl. The aqueous layer collected was alkalized by addition of potassium carbonate and then extracted with dichloromethane, the organic layer collected was washed with saturated aqueous solution of sodium chloride, dried over anhydrous sodium sulfate and concentrated under reduced pressure, thus giving 0.89 g (98 %) of ethyl 1-methyl-5,6,7,8-tetrahydroimidazo[1,5-a]pyridine-7-carboxylate.

Physicochemical Properties (i) NMR spectrum (CDCl₃) δ: 1.30 (3H, t, J=7Hz), 1.70–2.30 (5H, m), 2.15 (3H, s), 3.63–4.60 (4H, m), 7.25 (1H, s)

(ii) Mass spectrum (EI): m/z 208 (M+)

B. Hydrochloride of 1-methyl-5,6,7,8-tetrahydroimidazo[1,5-a ]pyridine-7-carboxylic acid

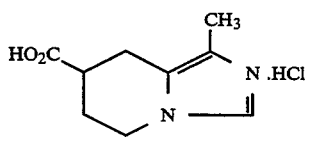

Hydrochloride of 1-methyl-5,6,7,8-tetrahydroimidazo[1,5-a]-pyridine-7-carboxylic acid was obtained in the same manner as in C of Reference Example 1 by using the compound obtained in A above.

Physicochemical Properties (i) NMR spectrum (DMSO-d₆) δ: 1.65–2.65 (2H, m), 2.22 (3H, s), 2.65–3.33 (3H, m), 3.90–4.62 (2H, m), 8.98 (1H, s)

(ii) Mass spectrum (EI): 180(M+, in the free form)

REFERENCE EXAMPLE 3

Ethyl 5,6,7,8-tetrahydroimidazo[1,2-a]pyridine-7-carboxylate

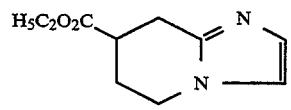

Ethyl 5,6,7,8-tetrahydroimidazo[1,2-a]pyridine-7-carboxylate was obtained in the same manner as in A and B of Reference Example 2 by using 2-imidazole-carbaldehyde as the starting material.

Physicochemical Properties (i) NMR spectrum(CDCl₃) δ: 1.30 (3H, t, J=7Hz), 1.80–2.60 (2H, m), 2.62–3.30 (3H, m), 3.80–4.55 (4H, m), 6.65–7.15 (2H, m)

(ii) Mass spectrum (EI): m/z 194(M+)

REFERENCE EXAMPLE 4

Hydrochloride of 5,6,7,8-tetrahydroimidazo[1,2-a]pyridine-6-carboxylic acid

A. Sulfate of Methyl Imidazo[1,2-a]Pyridine-6-Carboxylate

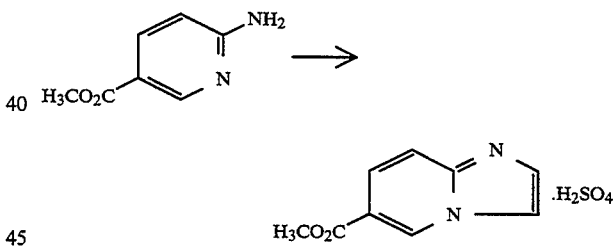

A solution of 12.5 g bromoacetaldehyde diethyl acetal in hydrochloric acid (prepared from 1.5 mg conc. HCl and 70 ml water) was stirred at 90° C. for 90 minutes, 3.30 g of methyl 6-aminonicotinate and 5 g of sodium bicarbonate were then added at room temperature, and the resulting mixture was heated at 60° C. for 30 minutes. The reaction mixture was cooled to room temperature, alkalized by addition of potassium carbonate and extracted with ethyl acetate. The organic layer collected was washed with saturated aqueous solution of sodium chloride, dried over anhydrous magnesium sulfate and concentrated to dryness under reduced pressure, the residue was dissolved in ethanol, concentrated sulfuric acid was added to the ethanolic solution, and the crystals thus formed were collected by filtration, thus giving 4.45 g (75 %) of sulfate of methyl imidazo[1,2-a]pyridine-6-carboxylate.

Physicochemical Properties (i) NMR spectrum (DMSO-d₆)
δ: 3.98 (3H, s), 8.09–8.44 (3H, m), 8.50 (1H, d, J=2 Hz), 9.66 (1H, d, J=1 Hz)

(ii) Mass spectrum (EI): m/z 176(M+, in the free form)

B. Methyl 5,6,7,8-tetrahydroimidazo[1,2-a]pyridine-6-carboxylate

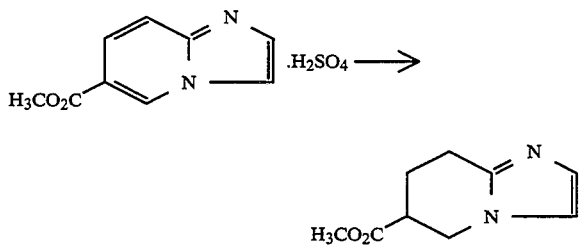

Methyl 5,6,7,8-[etrahydroimidazo[1,2-a]pyridine-6-carboxylate was obtained in the same manner as in B of Reference Example 1 by using the compound obtained in A above.

Physicochemical Properties (i) NMR spectrum(CDCl3) δ: 1.80–2.65 (2H, m), 2.76–3.35 (3H, m), 3.77 (3H, s), 4.18 (2H, d, J=7 Hz), 6.80 (1H, d, J=1 Hz), 6.98 (1H, d, J=1 Hz)
(ii) Mass spectrum (EI): m/z 180(M+)

C. Hydrochloride of 5,6,7,8-tetrahydroimidazo[1,2-a]pyridine-6-carboxylic acid

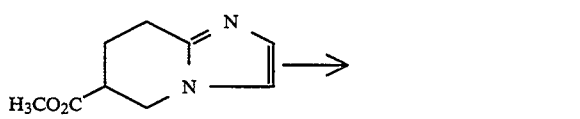

Hydrochloride of 5,6,7,8-tetrahydroimidazo[1,2-a]pyridine-6-carboxylic acid was obtained in the same manner as in C of Reference Example 1 by using the compound obtained in B above.

Physicochemical Properties (i) NMR spectrum (DMSO d6) δ: 1.75–2.60 (2H, m), 2.80–3.45 (3H, m), 3.95–4.65 (2H, m), 7.58 (1H, d, J=2 Hz), 7.64 (1H, d, J=2 Hz)
(ii) Mass spectrum (EI): 166(M+, in the free form)

EXAMPLE 1

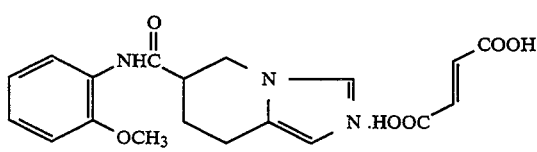

Fumarate of N-(2-Methoxyphenyl)-5,6,7,8-Tetrahydroimidazo[1,5-a]Pyridine-6-Carboxamide To 5 ml of acetonitrile, were added 0.30 g of 5,6,7,8-tetrahydroimidazo[1,5-a]pyridine-6-carboxylic acid hydrochloride and 0.22 ml of thionyl chloride, and the mixture was stirred at 60° C. for 30 minutes. The reaction mixture was concentrated to dryness under reduced pressure, 5 ml of acetonitrile was added to the residue, and 0.74 g of 2-anisidine was then added under ice-water cooling. The resulting mixture was stirred overnight at room temperature and concentrated to dryness under reduced pressure, water was added to the residue, and the pH was adjusted to about 4 by addition of dilute hydrochloric acid. This solution was washed with diethyl ether, and the pH was adjusted to about 9 by addition of potassium carbonate. The resulting solution was extracted with chloroform, the organic layer collected was dried over anhydrous magnesium sulfate, and the solvent was distilled off from the dried solution under reduced pressure. The residue was washed with diethyl ether, an equimolar amount of fumaric acid was added, and the mixture was recrystallized with methanol, thus giving 0.29 g of fumarate of N-(2-methoxyphenyl)-5,6,7,8-tetrahydroimidazo[1,5-a]pyridine-6-carboxamide having a melting point of 188°–189° C.

Physicochemical Properties (i) Elemental analysis (as C15H17N3O2·C4H4O4·0.1C-H3OH·0.45H2O)

|  | C(%) | H(%) | N(%) |
|---|---|---|---|
| Calcd. | 57.54 | 5.64 | 10.54 |
| Obsd. | 57.82 | 5.47 | 10.24 |

(ii) Mass spectrum (EI): m/z 271(M+, in the free from)

The following compounds were obtained in the same manner as in Example 1.

EXAMPLE 2

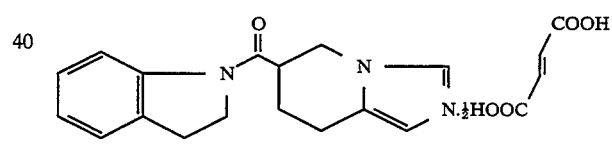

6-[(2,3-Dihydroindol-1-yl)carbonyl]-5,6,7,8-tetrahydroimadazo[1,5 a]pyridine·0.5fumarate Physicochemical Properties (i) Melting point: 206°–207° C. (methanol)
(ii) Elemental analysis (as C16H17N3O·0.5C4H4O4)

|  | C(%) | H(%) | N(%) |
|---|---|---|---|
| Calcd. | 66.45 | 5.89 | 12.91 |
| Obsd. | 66.13 | 5.84 | 12.70 |

(iii) Mass spectrum (HI): m/z 267(M+, in the free form)

EXAMPLE 3

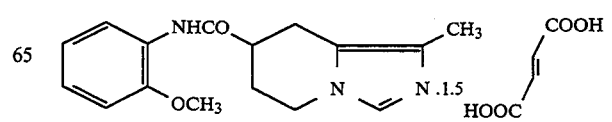

N-(o-Methoxyphenyl)-1-methyl-5,6,7,8-tetrahydroimidazo[1.5-a]pyridine-7-carboxamide·1.5fumarate Physicochemical Properties (i) Melting point: 192°–194° C. (methanol-acetonitrile)

(ii) Elemental analysis (as $C_{16}H_{19}N_3O_2 \cdot 1.5C_4H_4O_4$)

|  | C(%) | H(%) | N(%) |
|---|---|---|---|
| Calcd. | 57.51 | 5.48 | 9.15 |
| Obsd. | 57.61 | 5.55 | 9.45 |

(iii) Mass spectrum (EI): 285(M+, in the free form)

EXAMPLE 4

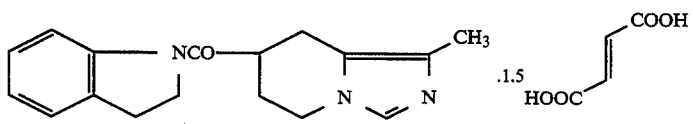

7-(2,3-dihydro1-Indolylcarbonyl)-1-methyl-5,6 7,8-tetrahydroimidazo[1,5-a]pyridine·1.5fumarate Physicochemical Properties (i) Melting point: 192°–194° C. (methanol-acetonitrile)

(ii) Elemental analysis (as $C_{17}H_{19}N_3O \cdot 1.5C_4H_4O_4$)

|  | C(%) | H(%) | N(%) |
|---|---|---|---|
| Calcd. | 60.65 | 5.53 | 9.23 |
| Obsd. | 60.56 | 5.47 | 9.23 |

(iii) Mass spectrum (EI): 281(M+, in the free form)

EXAMPLE 5

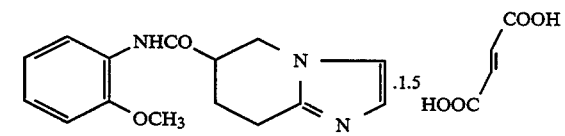

N-(o-Methoxyphenyl)-5,6,7,8-tetrahydroimidazo[1,2-a]-pyridine-6-carboxamide·1.5fumarate Physicochemical Properties (i) Melting point: 181°–183° C. (methanol-acetonitrile)

(ii) Elemental analysis (as $C_{15}H_{17}N_3O_2 \cdot 1.5C_4H_4O_4$)

|  | C(%) | H(%) | N(%) |
|---|---|---|---|
| Calcd. | 56.63 | 5.20 | 9.43 |
| Obsd. | 56.60 | 5.23 | 9.52 |

(iii) Mass spectrum (EI): 271(M+, in the free form)

EXAMPLE 6

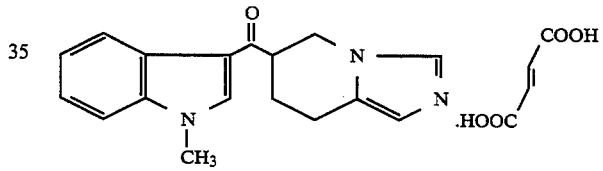

6-(2,3-dihydro1-Indolylcarbonyl)-5,6,7,8-tetrahydroimidazo[1,2-a]-pyridine

Physicochemical Properties (i) Melting point: 178°–180° C. (dichloromethane-hexane)

(ii) Elemental analysis (as $C_{16}H_{17}N_3O$)

|  | C(%) | H(%) | N(%) |
|---|---|---|---|
| Calcd. | 71.89 | 6.41 | 15.72 |
| Obsd. | 71.80 | 6.47 | 15.62 |

(iii) Mass spectrum (EI): 267(M+)

EXAMPLE 7

6-[(1-Methylindol-3-yl)carbonyl]-5,6,7,8-tetrahydroimidazo[1.5-a]pyridine·fumarate To 4 ml of acetonitrile, were added 0.41 g of hydrochloride of 5,6,7,8-tetrahydroimidazo[1,5-a]pyridine-6-carboxylic acid and 0.29 ml of thionyl chloride in that order, and the mixture was stirred at 80° C. for one hour and then concentrated to dryness under reduced pressure. The residue was suspended in 4 ml acetonitrile, this suspension was added to a suspension of 3.35 ml pyrrolidine in 4 ml acetonitrile at a temperature lower than 10° C., and the mixture was stirred at room temperature for one hour and then concentrated to dryness under reduced pressure. An aqueous solution of potassium carbonate was added to the residue, the mixture was extracted with chloroform containing a small amount of methanol, the organic layer collected was dried over anhydrous magnesium sulfate, and the dried solution was concentrated to dryness under reduced pressure (concentration after addition of toluene was repeated twice).

The residue was dissolved in ethanol, 0.5 ml of 4N-HCl solution in ethyl acetate was added to the ethanolic solution, and the mixture was concentrated to dryness under reduced pressure.

Dichloroethane (3 ml) and 1-methylindole (0.23 g) were added to the residue, 0.32 g of phosphorus oxychloride was then added, and the mixture was stirred at 80° C. for four hours. The solvent was distilled off from the reaction mixture under reduced pressure, an aqueous solution of potassium carbonate was then added, and the mixture was extracted with chloroform. The solvent was distilled off from the collected organic layer under reduced pressure, the residue was subjected to column chromatography (silica gel, chloroform-methanol), and the eluate was treated with a calculated amount of fumaric acid in methanol, thus giving 0.08 g of 6-[(1-methylindol-3-yl)carbonyl]-5,6,7,8-tetrahydroimidazo[1,5-a]pyridine·fumarate having a melting point of 183°–185° C.

Physicochemical Properties (i) Elemental analysis (as $C_{17}H_{17}N_3O \cdot C_4H_4O_4 \cdot 0.3CH_3OH$)

|  | C(%) | H(%) | N(%) |
|---|---|---|---|
| Calcd. | 63.17 | 5.52 | 10.37 |
| Obsd. | 62.97 | 5.44 | 10.35 |

(ii) Mass spectrum (EI): m/z 279(M+, in the free form)

EXAMPLE 8

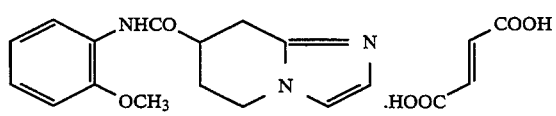

N-(o-Methoxyphenyl)-5,6,7,8-tetrahydroimidazo[1,2-a]pyridin-7-carboxamide·fumarate A solution of 0.18 g ethyl 5,6,7,8-tetrahydroimidazo[1,2-a]pyridine-7-carboxylate in 10 ml of 3N-HCl was heated overnight under reflux, the reaction mixture was concentrated to dryness under reduced pressure, and the residue was dried, thus giving 0.18 g of 5,6,7,8-tetrahydroimidazo[1,2-a]pyridine-7-carboxylic acid·hydrochloride.

The mixture of this hydrochloride with 1 ml thionyl chloride was heated at 60° C. for 20 minutes, the reaction mixture was again concentrated to dryness, 3 ml of dichloromethane and 0.6 ml o-anisidine were added to the residue in that order at room temperature, and the mixture was stirred for one hour. After addition of dichloromethane, the reaction mixture was extracted with 0.5N-HCl, and the aqueous layer collected was alkalized by adding potassium carbonate and extracted with dichloromethane. The organic layer collected was washed with saturated aqueous solution of sodium chloride, dried over anhydrous sodium sulfate and concentrated to dryness under reduced pressure, and the residue was subjected to chromatography on silica gel (10 g). Elution with 2% methanol-chloroform gave 0.11 g of N-o-methoxyphenyl-5,6,7,8-tetrahydroimidazo[1,2-a]pyridine-7-carboxamide, which was inverted into its fumarate by reaction with a calculated amount of fumaric acid.

(i) Melting point: 151°–153° C. (methanol-acetonitrile)

(ii) Elemental analysis (as $C_{15}H_{17}N_3O_2 \cdot C_4H_4O_4$)

|  | C(%) | H(%) | N(%) |
|---|---|---|---|
| Calcd. | 58.91 | 5.46 | 10.85 |

-continued

|  | C(%) | H(%) | N(%) |
|---|---|---|---|
| Obsd. | 59.01 | 5.47 | 11.21 |

(iii) Mass spectrum (EI): 271(M+, in the free form)

What is claimed is:

1. Tetrahydroimidazopyridine derivative represented by the following formula,

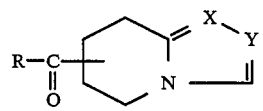

wherein either one of X and Y is nitrogen and the other one is a radical represented by the formula =C(R¹)—; and R is a radical of the formula

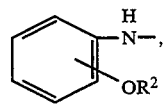

a radical of the formula

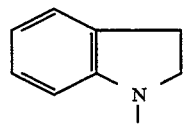

or a radical of the formula

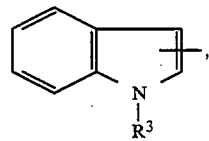

in which R¹, R² and R³ are same or different hydrogen atom or a lower alkyl group, and salts thereof.

2. Tetrahydroimidazopyridine derivative represented by the following formula,

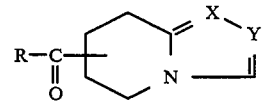

wherein either one of X and Y is nitrogen atom and the other one is a radical represented by the formula =C(R¹)—; and R is a radical of the formula

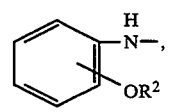

a radical of the formula

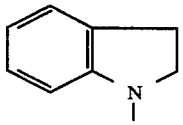

or a radical of the formula

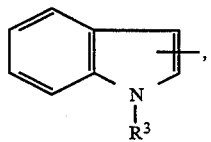

in which $R^1$, $R^2$ and $R^3$ are same or different and represent hydrogen or a $C_1$–$C_6$ alkyl group, and salts thereof.

3. A compound according to claim 1 wherein R is:

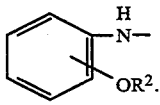

4. A compound according to claim 1 wherein R is:

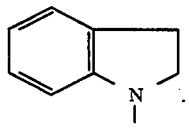

5. A compound according to claim 1 wherein $R^1$, $R^2$ and $R^3$ are selected from the group consisting of hydrogen and $C_1$–$C_3$ alkyl groups.

6. A compound according to claim 1 which is a member selected from the group consisting of
N-(2-methoxyphenyl)-5,6,7,8-tetrahydroimidazol[1,5-a]pyridine-6-carboxamide;
6-[(2,3-dihydroindol-1-yl)carbonyl)-5,6,7,8-tetrahydroimidazol [1,5-a]pyridine;
N-(o-methoxyphenyl)-1-methyl-5,6,7,8-tetrahydroimidazol[1,5-a]pyridine-7-carboxamide;
7-(2,3-dihydro-1-indolylcarbonyl)-1-methyl-5,6,7,8-tetrahydroimidazo[1,5-a]pyridine
N-(o-methoxyphenyl)-5,6,7,8-tetrahydroimidazol[1,2-a]-pyridine-6-carboxamide
6-(2,3-dihydro1-indolylcarbonyl)-5,6,7,8-tetrahydroimidazol[1,2-a]-pyridine;
6-[1-methylindol-3-yl)carbonyl]-5,6,7,8-tetrahydroimidazol[1,5-a]pyridine; and
N-(o-methoxyphenyl)-5,6,7,8-tetrahydroimidazol[1,2-a]pyridin-7-carboxamide;
or salts thereof.

7. A pharmaceutical composition containing a compound according to claim 1 and pharmaceutically acceptable carrier.

8. A pharmaceutical composition containing a compound according to claim 2 and a pharmaceutically acceptable carrier.

9. A pharmaceutical composition containing a compound according to claim 3 and a pharmaceutically acceptable carrier.

* * * * *